(12) United States Patent
Kurosawa et al.

(10) Patent No.: US 9,057,708 B2
(45) Date of Patent: Jun. 16, 2015

(54) INSPECTION EQUIPMENT FOR MOUTH SECTION OF BOTTLE-CAN

(75) Inventors: Akio Kurosawa, Neyagawa (JP); Tadayuki Sota, Neyagawa (JP)

(73) Assignees: Kurashiki Boseki Kabushiki Kaisha, Okayama (JP); Universal Can Corporation, Tokyo (JP)

( * ) Notice: Subject to any disclaimer, the term of this patent is extended or adjusted under 35 U.S.C. 154(b) by 0 days.

(21) Appl. No.: 14/123,986

(22) PCT Filed: Jun. 4, 2012

(86) PCT No.: PCT/JP2012/064409
§ 371 (c)(1),
(2), (4) Date: Dec. 5, 2013

(87) PCT Pub. No.: WO2012/169470
PCT Pub. Date: Dec. 13, 2012

(65) Prior Publication Data
US 2014/0098365 A1 Apr. 10, 2014

(30) Foreign Application Priority Data
Jun. 6, 2011 (JP) .................................. 2011-126216

(51) Int. Cl.
*G01N 21/00* (2006.01)
*G01N 21/90* (2006.01)

(52) U.S. Cl.
CPC .......... *G01N 21/909* (2013.01); *G01N 21/9054* (2013.01)

(58) Field of Classification Search
CPC .... C23C 16/045; C23C 16/401; C23C 16/505
USPC ......... 356/240, 240.1, 237.1, 239.5; 348/125, 348/127, 128, 131, 135, 142
See application file for complete search history.

(56) References Cited

U.S. PATENT DOCUMENTS

| 4,437,985 A * | 3/1984 | Hinds et al. ................... 356/428 |
| 6,618,495 B1 * | 9/2003 | Furnas ........................... 382/142 |
| 6,903,814 B1 * | 6/2005 | Juvinall et al. ................ 356/428 |

FOREIGN PATENT DOCUMENTS

| JP | 2004-083128 A | 3/2004 |
| JP | 2004-264132 A | 9/2004 |
| JP | 2007-084081 A | 4/2007 |

OTHER PUBLICATIONS

International Search Report dated Sep. 4, 2012, issued for PCT/JP2012/064409.

*Primary Examiner* — Kara E Geisel
*Assistant Examiner* — Iyabo S Alli
(74) *Attorney, Agent, or Firm* — Locke Lord LLP

(57) ABSTRACT

Inspection equipment for mouth section of bottle-can, including: a rotating device which holds and rotates the bottle-can around a can-axis; a first illumination device which irradiates a first illumination light toward the curl portion in an imaging area; a second illumination device which irradiates a second illumination light having a different light color from that of the first illumination light toward the curl portion from an opposite side to the first illumination light with the imaging area therebetween; a third illumination device which irradiates a third illumination light having a different light color along an intersecting direction with the first and second illumination lights; an imaging device which is disposed toward the imaging area and obtains an inspection image including reflected lights at the curl portion; and an asperity-recognition device which detects an edge position of the curl portion based on the reflected light of the third illumination light.

9 Claims, 9 Drawing Sheets

INSPECTION EQUIPMENT FOR MOUTH SECTION OF BOTTLE-CAN

CROSS REFERENCE TO RELATED APPLICATIONS

This application is related to two co-pending applications: "INSPECTION EQUIPMENT FOR SCREW PART OF BOTTLE-CAN" filed even date herewith in the names of Akio Kurosawa and Tadayuki Sota as a national phase entry of PCT/JP2012/064411 and "INSPECTION METHOD AND INSPECTION EQUIPMENT FOR MOUTH SECTION OF BOTTLE-CAN" filed even date herewith in the names of Akio Kurosawa, Tadayuki Sota and Tadafumi Hirano as a national phase entry of PCT/JP2012/064410; which applications are assigned to the assignee of the present application and all incorporated by reference herein.

BACKGROUND OF THE INVENTION

1. Field of the Invention

The present invention relates to inspection equipment for a mouth section of a bottle can.

Priority is claimed on Japanese Patent Application No. 2011-126216, filed Jun. 6, 2011, the content of which is incorporated herein by reference.

2. Description of the Related Art

A can having a bottle-shape of aluminum alloy in which a cap is screwed on a mouthpiece having a screw is known as a container filled with contents such as drinks. The can is manufactured by: forming an aluminum alloy sheet into a closed-end cylindrical body which has a bottom plate and a cylindrical side surface in one piece by performing drawing processing and ironing processing (i.e., DI forming); coating an inner surface and an outer surface of the close-ended cylindrical body; forming a shoulder and the mouthpiece by performing so-called neck-in processing on an opening portion; and performing screw-forming processing, curl-forming processing and the like on the mouthpiece.

An inner coating in the can is formed by thermo-setting resin such as epoxy-acrylic resin, polyester resin or the like in order to make corrosion resistance and so on to the can with respect to content of the can (refer to Patent Document 1). The inner coating is formed by spraying paint on an inner surface of the can after the drawing and ironing processing before the neck-in processing. However, the paint may scatter around or may cleave to the outer surface of the can and tiny protrusions are formed, so that the protrusions may preface with corrugations when the neck-in processing is performed.

A curl portion is formed by folding an upper end of the mouthpiece outward and the inner coating is formed an outer surface of the curl portion. The can is hermetically sealed by attaching a cap so as to press a liner to the curl portion (refer to Patent Document 2). Therefore, if asperity such as the aforementioned corrugations by the paint is formed on the surface of the curl portion, especially on a top surface, or deformation such as a pit is formed on the curl portion, the content may be leaked. However, there is a case in which the asperity is formed on the surface of the curl portion by the inner coating being crumpled when the mouth section and the curl portion are formed.

Therefore, it is important that the curl portion is not deformed and the asperity such as the corrugations and the like are not formed on the top surface of the curl portion. Furthermore, in case of the asperity is formed, it is expected that the asperity is detected in an inspection process and reliably excluded as a defective.

For example, as a detection method for detecting fine asperity (e.g., corrugation or the like) formed on the outer surface, a detection method in which a can-body is irradiated obliquely to a tangent plane (i.e., a plane along a tangent line of the outer surface) so that corrugations are detected by observing reflection or shade of the corrugations along the tangent plane is suggested (refer to Patent Document 3).

PRIOR ART DOCUMENT

Patent Document

Patent Document 1: Japanese Unexamined Patent Application, First Publication No. 2007-84081
Patent Document 2: Japanese Unexamined Patent Application, First Publication No. 2004-83128
Patent Document 3: Japanese Unexamined Patent Application, First Publication No. 2004-264132

SUMMARY OF THE INVENTION

Problems to be Solved by the Invention

In the bottle-can, the asperity on the curl portion should be reliably detected since it causes liquid leakage. On the other hand, since color figure without asperity such as punch-figure or blot by DI forming do not affect sealing performance, it is not necessary to exclude a bottle-can having such the color figure. If the color figure is detected as the asperity, non-defective may be excluded as a defective product, so that yield may be deteriorated.

In the inspection method described in Patent Document 3, since the corrugations are detected by checking shade by illumination light for the can, there is a bare possibility that the color figure is detected as defective by this method. However, since it is necessary to position the can with respect to the illumination light and a camera, a correct detection result may be hard to be obtained if the can is receded from a detection position.

The present invention is achieved in consideration of the above circumstances, and has an object to reliably detect only a defective product which may cause liquid leakage or the like in a mouth section inspection of a bottle-can.

Means for Solving the Problem

The present invention is inspection equipment for a mouth section of a bottle-can, with respect to the bottle-can having the cylindrical mouth section in which a curl portion is formed by curling an open end thereof for a cap with a liner to be put on, by taking an image of an imaging area which is set to include a part of the curl portion for detecting asperity at the curl portion, having: a rotating device which holds and rotates the bottle-can around a can-axis; a first illumination device which irradiates a first illumination light substantially along a tangential direction of a cylindrical surface of the mouth section with respect toward the curl portion in the imaging area; a second illumination device which irradiates a second illumination light having a different light color from that of the first illumination light toward a part in which the first illumination light is irradiated on the curl portion from an opposite side to the first illumination light with the imaging area therebetween along substantially the tangential direction of the cylindrical surface of the mouth section; a third illumination device which irradiates a third illumination light having a different light color from that of the first illumination light and the second illumination light toward the part in which the first illumination light and the second illumination light are irradiated on the curl portion along an intersecting direction with the first illumination light and the second illumination light; an imaging device which is disposed toward the imaging area and obtains an inspection image including reflected lights at the curl portion; and an asperity-recognition device which detects an edge position of the curl portion based on a imaging result of the reflected light of the third illumination light, specifies the curl portion by referring the edge position, and detects the asperity at the curl position based on imaging results of the reflected lights of the first illumination light and the second illumination light existing in the inspection image.

According to the inspection equipment, the illumination lights with two colors are irradiated from different directions toward the curl portion in the imaging area, so that a reflected light by the asperity obstructing the illumination lights is taken as a stripe image of two colors in accordance with the light colors of the illumination lights. On the other hand, the reflected light by a roll-figure, a punch-figure, blot or the like without asperity does not form a stripe, but is taken as an image of light and shade of mixed color of the illumination lights. As a result, the asperity which may cause the liquid leakage can be reliably detected, to and the color-figure is not misidentified as the asperity. Furthermore, the illumination color having the different color is irradiated from the different direction, it is easy to specify the curl portion in the inspection image; and dimples or deformation of the curl portion can be detected since the form of the curl portion is clarified.

Moreover, according to the present inspection equipment, the asperity is detected by the color of the reflected light. Therefore, if the position of the mouth section is receded from the prescribed imaging area by the illumination lights and the imaging device, at least the illumination lights are irradiated toward the curl portion and the illuminated curl portion is positioned in the imaging area, the asperity of the curl portion can be detected. Accordingly, it is not necessary to control the position of the bottle-can precisely, so that a structure of the inspection equipment can be simplified.

Furthermore, by rotating the bottle-can around the can-axis, a whole circumference of the curl portion can be scanned. In a case in which the can-axis is deviated form a rotating axis of the rotating device, even though the curl portion is moved in the inspection image, the curl portion can be specified by detecting the edge position of the curl portion, so that the curl portion can be reliably inspected.

Accordingly, according to the inspection equipment for a mouth section of a bottle-can, only defective cans which may cause the liquid leakage or the like are reliably detected, reliable inspection can be operated without deteriorating a yield.

In the inspection equipment for a mouth section of a bottle-can, a structure in which the imaging area is set at an external circumferential surface of the curl portion can be applied. In this case, at the top surface of the curl portion, the asperity which may cause the liquid leakage or the like can be detect, and especially, the asperity extending along a radial direction can be detected without fail. Furthermore, if the third illumination light is irradiated diagonally toward the external circumferential surface, it is possible to detect the asperity extending along an axial direction at the external circumferential direction.

Alternatively, in the present inspection equipment for mouth section, a structure in which the imaging area is set at an external circumferential surface of the curl portion can be applied. In this case, the asperity at a side surface of the curl portion can be detected in distinction from the color-figure; and also deformation of the top surface can be detected.

Moreover, in the present inspection equipment for mouth section, a structure in which a plurality of sets of the first illumination device and the second illumination device are provided can be applied. For example, in a case in which the top surface of the curl portion is bent convexly, if a set of the illumination devices irradiates the illumination light toward the top surface only from outer peripheral side of the mouth section, the illumination light cannot reach an inner surface side of the top surface of the curl portion, so that this area is hard to be inspected. On the other hand, for example, in a case in which two sets of the illumination devices are provided so as to irradiate each of the illumination lights from the inner peripheral side and the outer peripheral side of the mouth section, the whole top surface of the curl portion can be illuminated and the asperity can be easily detected.

Effects of the Invention

According to the inspection equipment for mouth section of bottle-can of the present invention, by irradiating the illumination lights having the different colors from the different directions, since the mouth section is correctly specified in the inspection image and the color-figure without the asperity is not detected as the defect, the asperity can be reliably detected. As a result, the yield is not deteriorated, and it is possible to reliably eliminate only the defective product which may cause the liquid leakage.

DETAILED DESCRIPTION OF THE INVENTION

Figure 1:
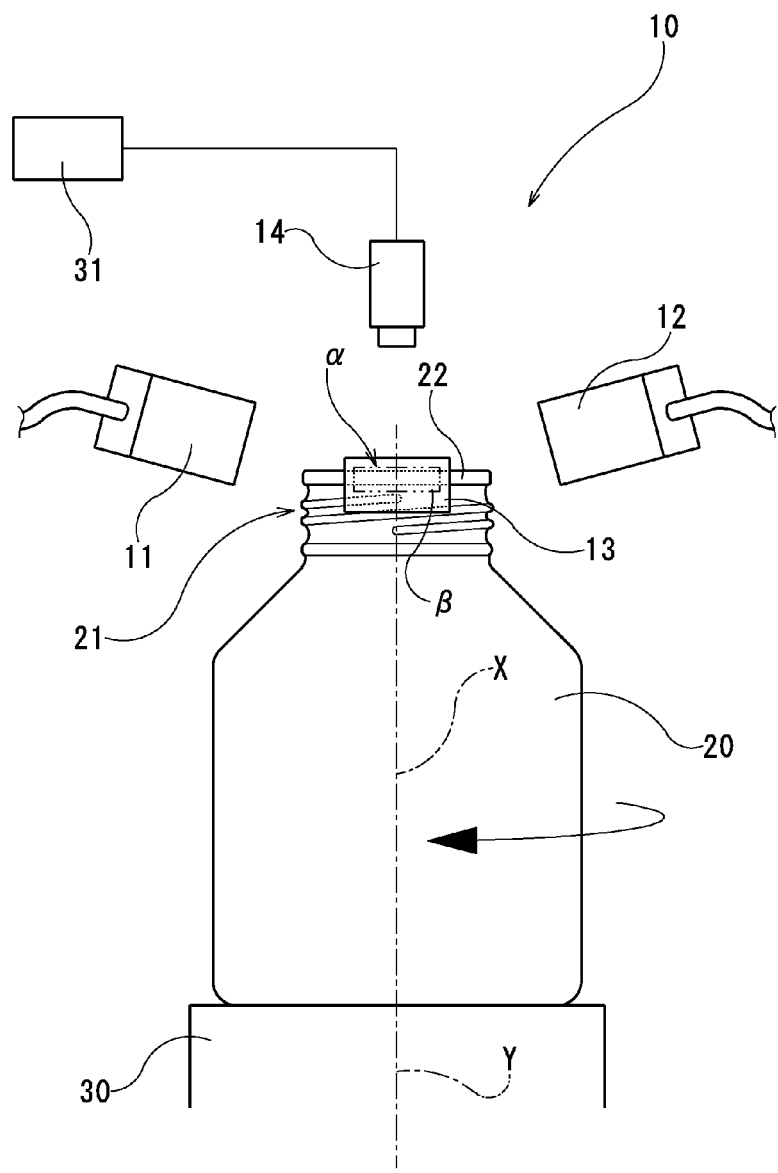
FIG. 1 It is a side view showing inspection equipment for mouth section of bottle-can according to the present invention.

Below, inspection equipment for mouth section of bottle-can according to the present invention will be described with drawings. Inspection equipment 10 for mouth section of bottle-can (hereinafter, "inspection equipment") of the present invention is equipment, with respect to a bottle-can 20 having a cylindrical mouth section 21 in which a curl portion 22 is formed by curling an open end thereof for a cap with a liner (not illustrated) to be put on as shown in FIG. 1, for detecting asperity at the curl portion 22 in an imaging area α which is set to include a part of the curl portion 22 (i.e., a part of a top surface in this embodiment) as shown in FIG. 2.

Inspection equipment 10 is provided with: a rotating device 30 which holds and rotates a bottle-can 20 around a can-axis X; a first illumination device 11 which irradiates a red first illumination light R toward a curl portion 22 in an imaging area α; a second illumination device 12 which irradiates a blue second illumination B toward the curl portion 22 in the imaging area α; a third illumination device 13 which irradiates a green third illumination light G toward a part in which the first illumination light R and the second illumination light B are irradiated on the curl portion 22; an imaging device 14 which obtains an inspection image including reflected lights at the curl portion 22; and an asperity-recognition device 31 which detect an edge position of the curl portion 22 based on an imaging result of a reflected light "g" of the third illumination light G, specifies a mouth section 21 by referring the edge position, and detects asperity at the curl portion 22 in the inspection image.

Figure 2:
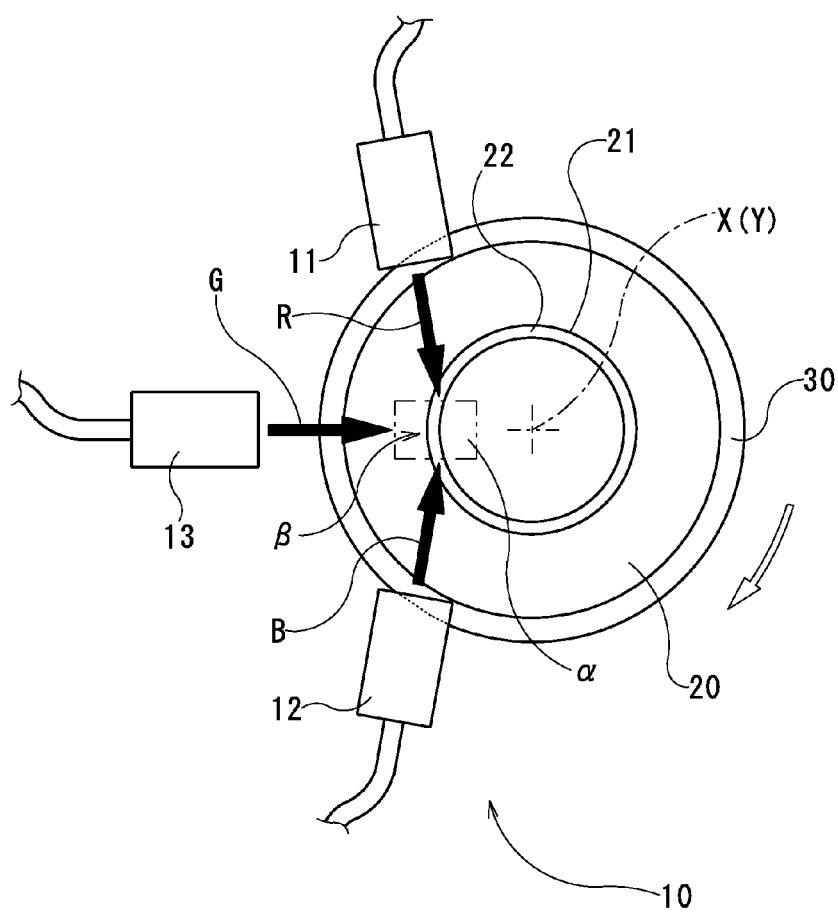
FIG. 2 It is a top view of the inspection equipment shown in FIG. 1.

In the inspection equipment 10, the imaging area α is set to include a top surface of the curl portion 22; and the first illumination device 11 and the second illumination device 12 are disposed so that the first illumination light R and the second illumination light B are irradiated toward the mouth section 21 (i.e., a part of the top surface of the curl portion 22) in the imaging area α (FIG. 2). The third illumination device 13 is disposed so as to irradiate the third illumination light G toward an external circumferential surface (i.e., an edge-detection area β) which is continued and bent from a part in which the first illumination light R and the second illumination light B are irradiated in the curl portion 22.

As shown in FIG. 1 and FIG. 2, the first illumination device 11 is arranged on a side of the mouth section 21 of the bottle-can 20, and irradiates the red first illumination light R toward the top surface of the curl portion 22 in the imaging area α along substantially a tangential direction of a cylindrical surface of the mouth section 21.

As shown in FIG. 1 and FIG. 2, the second illumination device 12 is arranged on an opposite side of the first illumination device 11 with the imaging area α therebetween, and irradiates the second illumination light B having blue color which is different light color from that of the red first illumination light R toward a part in which the first illumination light R is irradiated on the curl portion 22 along substantially the tangential direction of the cylindrical surface of the mouth section 21.

That is to say, in the curl portion 22 in the imaging area α, as shown in FIG. 2, the first illumination light R and the second illumination light B are irradiated double from the different directions by the first illumination device 11 and the second illumination device 12.

In the bottle-can 20, the edge-detection area β is continued and bent from the imaging area α, and set so as to including the external circumferential surface of the curl portion 22. As shown in FIG. 1 and FIG. 2, the third illumination device 13 is arranged on the side of the mouth section 21 of the bottle-can 20, irradiates the green third illumination light G having the different light color from that of the first illumination light R and the second illumination light B along substantially an intersecting direction with the first illumination light R and the second illumination light B, that is to say, along substantially orthogonal to the tangential direction of the cylindrical surface of the mouth section 21 toward an external circumferential surface of the curl portion 22 in the edge-detection area β.

With respect to the illumination devices 11 to 13 and the imaging device 14, by rotating the bottle-can 20 around the can-axis X by the rotating device 30 while obtaining an inspection image, a whole circumference of the mouth section 21 is scanned, so that a scanned image S including reflected lights at the curl portion 22 in an inspection image I can be imaged. The inspection image I and the scanned image S are entered to an asperity-recognition device 31 connected with the imaging device 14, and utilized for detecting an asperity of the curl portion 22.

The imaging device 14 is, as shown in FIG. 1, disposed above the mouth section 21 of the bottle-can 20, toward the imaging area α, that is to say, toward the top surface of the curl portion 22, and can image the inspection image I including the reflected lights at the curl portion 22.

The asperity-recognition device 31 which is connected to the imaging device 14 fetches the inspection image I which is obtained by the imaging device 14, detects an edge position of the curl portion 22 based on an imaging result of the reflect light "g" of the third illumination light G in the inspection image I, specifies the curl portion 22 by referring the edge position, and detects asperity of the curl portion 22 based on an imaging result of reflected lights "r" and "b" of the first illumination light R and the second illumination light B existing in the inspection image I.

Figure 3:
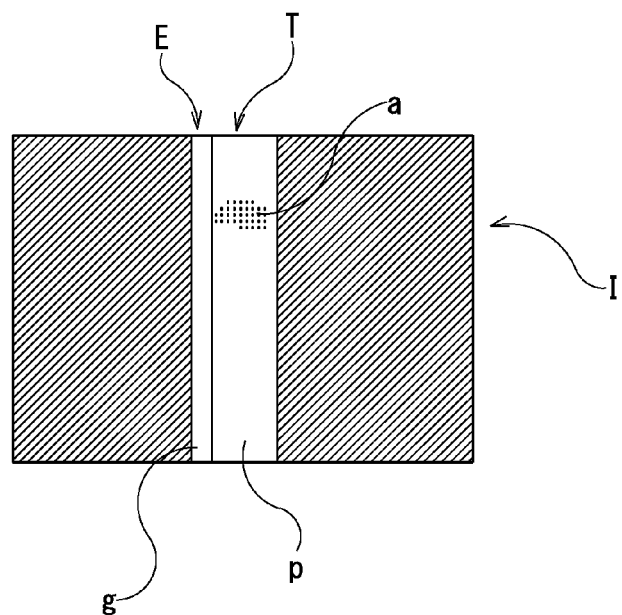
FIG. 3 It is an inspection view showing a curl portion in which asperity is not formed in the inspection equipment shown in FIG. 1.

In the inspection equipment 10 constructed as above, as shown in FIG. 3, in the inspection image I obtained by the imaging device 14, the reflected light "g" of the third illumination light G at the edge-detection area β is detected. The asperity-recognition device 31 detects the edge position E of the curl portion 22 by means of the reflected light "g", and specifies the curl portion 22 in the inspection image I by referring the edge position E.

More specifically, by a computer (not illustrated) which fetches the inspection image I, the image of the reflected light "g" of the third illumination light G is followed, and the image position thereof is regarded as the edge position E of the curl portion 22, so that an area having a prescribed width from the edge position E is calculated as a top surface T of the to curl portion 22. Then, an image of the reflected light "r" of the first illumination light R and an image of the reflected light "b" of the second illumination light B existing on the top surface T of the curl portion 22 are recognized; from the result, the asperity is discerned. If a displacement of the image of the reflected light "g" of the third illumination light G exceeds a specified displacement along a radial direction of the curl portion 22, it is judged as a defect having an edge-failure.

Here, the recognition of the asperity will be specifically explained. If the curl portion 22 is even without asperity, an equable reflected light "p" is imaged on the top surface T in the inspection image I so as to have purple color which is mixed color of the first illumination light R and the second illumination light B (FIG. 3). Also, the reflected light "p" at a part "a" of a color figure such as a flat roll-figure, a flat punch-figure, a flat blot or the like is purple but shading thereof is different.

Figure 4:
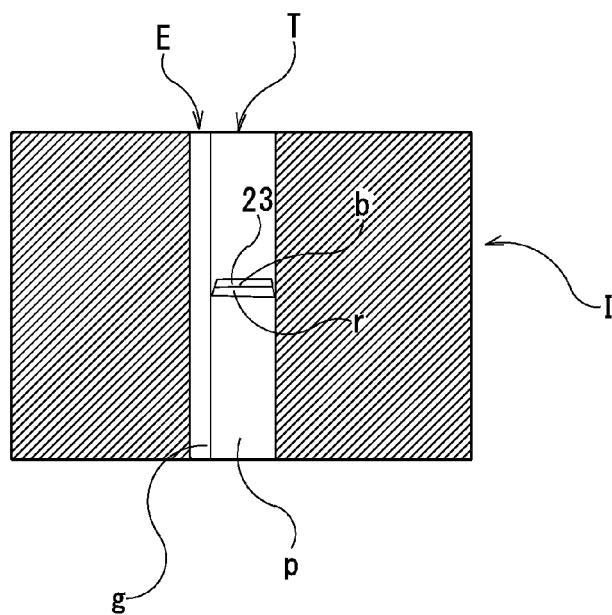
FIG. 4 It shows an inspection image of the curl portion in which the asperity is formed on the top surface in the inspection equipment shown in FIG. 1.

On the other hand, in a case in which asperity (e.g., a dimple 23) which changes a reflection direction of the illumination lights is formed on the curl portion 22, the first illumination light R and the second illumination light B do not reflected likewise since irradiated from the different direction, as shown in FIG. 4, a red reflected light "r" or a blue reflected light "b" is occurred in accordance with a shape of the dimple 23. By detecting the reflected lights "r" and "b" by the asperity-recognition device 31, it can be discovered that the asperity such as the dimple 23 is formed on the curl portion 22. Additionally, since the irradiation directions of the first illumination light R and the second illumination light B are substantially along the tangential direction of the cylindrical surface of the mouth section 21, the dimple 23 which is elongated along the radial direction of the bottle-can 20 on the curl portion 22 is easily detected.

Figure 5:
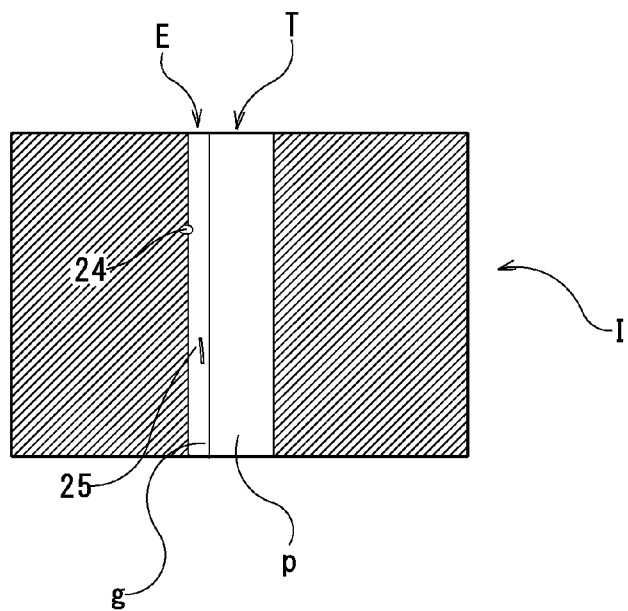
FIG. 5 It shows an inspection image of the curl portion in which a pit and a flaw are formed in the inspection equipment shown in FIG. 1.

The third-illumination light G is irradiated toward the edge-detection area β and reflected, and detected as the green reflected light "g" fringing an outer peripheral side of the curl portion 22, so that it is utilized as a guide for specifying the curl portion 22. However, in a case in which asperity such as a pit 24 is formed on an edge portion of the curl portion 22, as shown in FIG. 5, the reflected light "g" having a shape in accordance with a shape of the pit 24 appears, so that it is possible to detect the pit 24 and the like formed on the edge portion of the curl portion 22 by detecting the reflected light "g" having such a shape.

Figure 6:
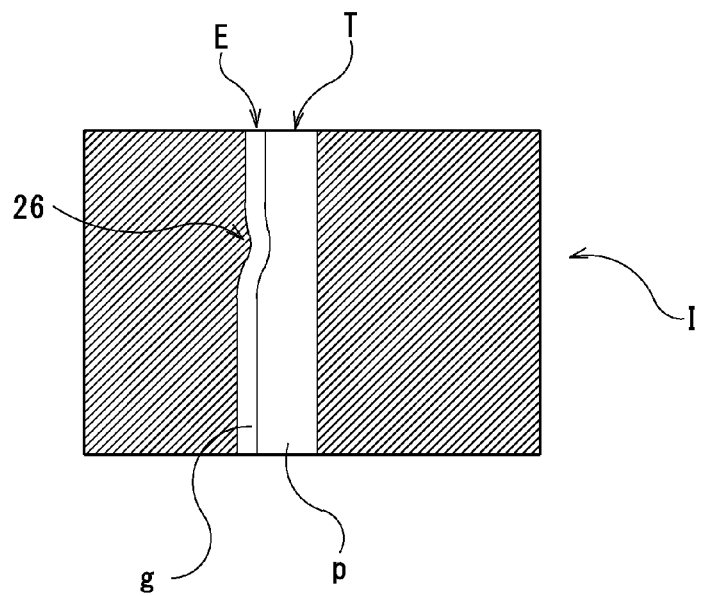
FIG. 6 It shows an inspection image of the curl portion in which a bent portion is formed on an external circumferential surface thereof in the inspection equipment shown in FIG. 1.

Furthermore, the asperity such as a flaw 25 formed on the edge portion of the curl portion 22 causes the third illumination light G to diffuse, so that by detecting such the diffusion, the flaw 25 on the external circumferential surface of the curl portion 22 can be detected. Moreover, in a case in which a partial bent portion 26 is formed as shown in FIG. 6, because the reflected light "g" in the edge-detection area 3 shows a bent shape in accordance with the shape of the bent portion 26, it is possible to detect the bent portion 26 of the curl portion 22 by detecting such the shape.

In the inspection equipment 10, by rotating the bottle-can 20 by the rotating device 30 with respect to the illumination devices 11 to 13 and the imaging device 14, so that a whole circumference of the mouth section 21 is scanned and the scanned image S can be obtained. At this time, if the can-axis X of the bottle-can 20 is deviated from a rotating axis Y of the rotating device 30, along with the rotation of the bottle-can 20, as shown in FIG. 7, the position of the curl portion 22 winds in the inspection image imaged by the imaging device 14, so that it is hard to detect a defective such as the bend at the curl portion 22.

However, in the inspection equipment 10, since the green reflected light "g" from the edge-detection area β indicates the edge position E of the curl portion 22, by following this reflected light "g" (i.e., the edge position E), the inspection can be performed while specifying the curl portion 22. Furthermore, by detecting a partial deformation 27 of the green reflected light "g", the defective such as the bent deformation of the like of the curl portion 22 can be detected.

Figure 7:
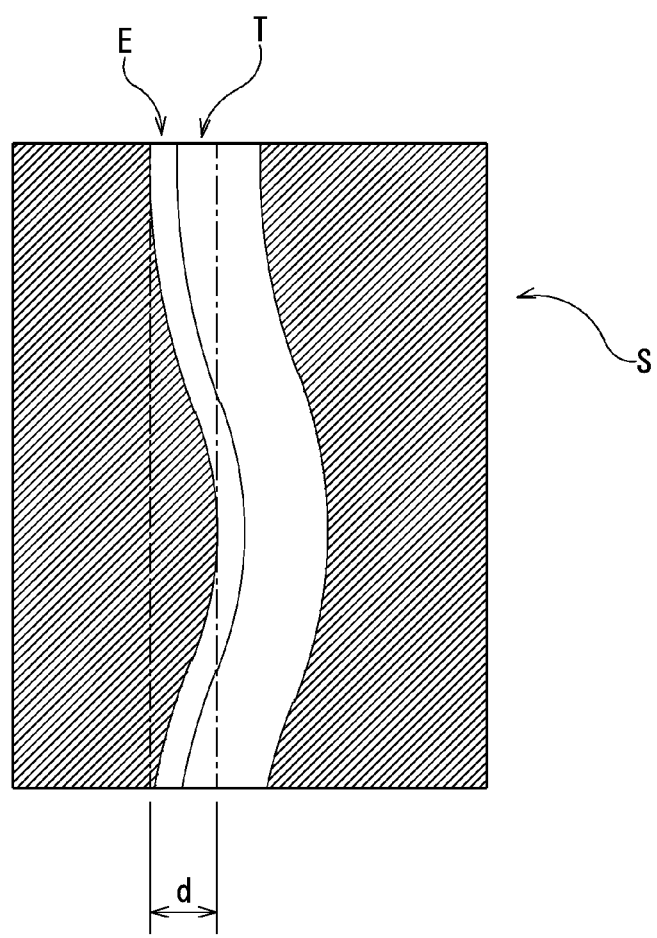
FIG. 7 It shows a scanned image which is obtained by imaging the curl portion while rotating an eccentric bottle-can from a rotating center in the inspection equipment shown in FIG. 1.
Figure 8:
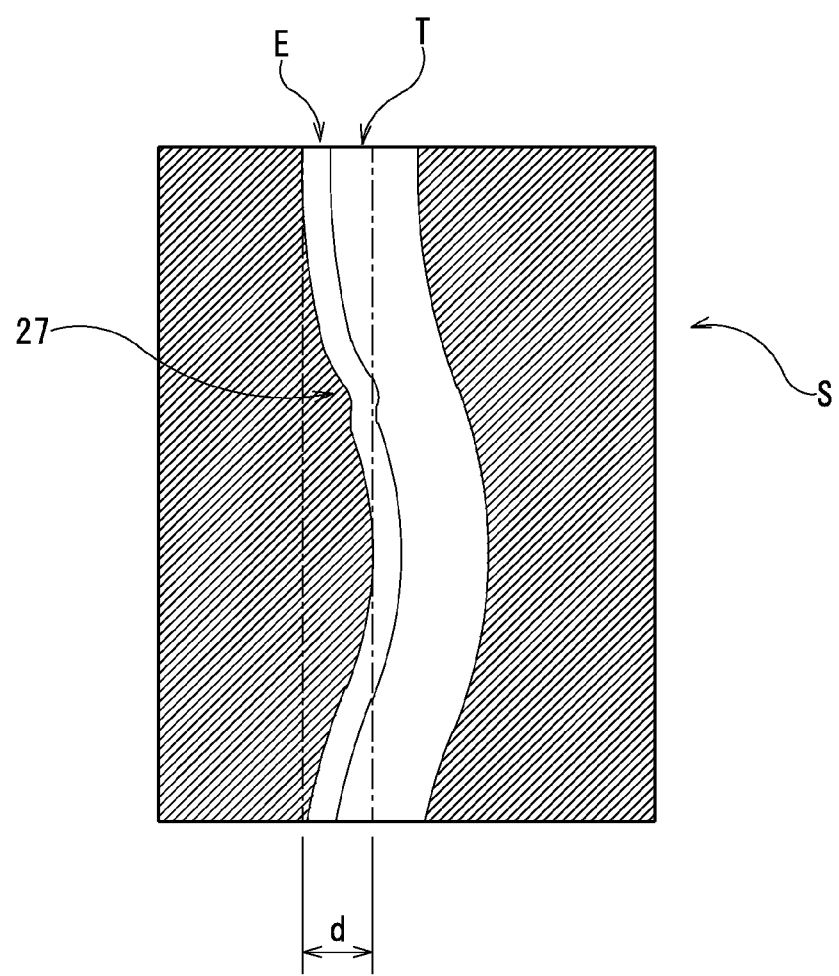
FIG. 8 It shows a scanned image which is obtained by imaging the curl portion while rotating an eccentric bottle-can from a rotating center in a case in which a dimple is formed on an external circumferential part of the curl portion in the inspection equipment shown in FIG. 1.

The scanned image S of the mouth section 21 obtained by imaging the bottle-can 20 while rotating is shown in FIG. 7 and FIG. 8. In the scanned image S, in a case in which the can-axis X is deviated at a distance "d" from the rotating axis Y of the rotating device 30, the edge position E meanders gently with a width "d" equivalent to the deviation distance (FIG. 7). On the other hand, in a case in which the mouth section 21 is deformed, as shown in FIG. 8, a local deformation 27 having a shape clearly different from the bent shape of the whole of the edge position E. Accordingly, since the bent portion of the curl portion 22 can be easily detected by detecting the deformation 27, a defective shape can be reliably detected while precisely recognizing the curl portion 22 even though the bottle-can 20 is rotated eccentrically.

Here, the detection of the asperity in the inspection image I (the scanned image S) will be explained with referring FIG. 9. If the surface of the curl portion 22 is flat, the reflected light "r" of the red first illumination light R and the reflected light "b" of the blue second illumination light B are mixed and incident into the imaging device 14, and the purple reflected light "p" is detected. As for the blot adhering to the curl portion 22 and the color-figure without asperity such as the punch-figure, since the first illumination light R and the second illumination light B are reflected, the purple reflected light "p" is detected. However, if the asperity such as the dimple 23 which prevents the incidence of the illumination lights R and B is formed on the curl portion 22, since the illumination lights R and B are irradiated from the different directions, there is an area only one of the reflected lights of the illumination light is detected by the imaging device 14. Therefore, by detecting the reflected light "b" or "r" which is not mixed color, only the asperity can be detected without detecting the color-figure.

Figure 9:
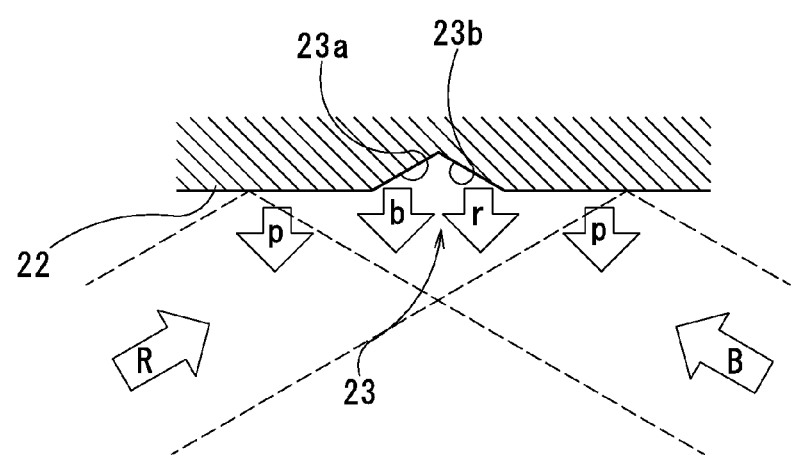
FIG. 9 It is a schematic view showing a reflection state of illumination lights having two colors at asperity in the inspection equipment shown in FIG. 1.
Figure 9:
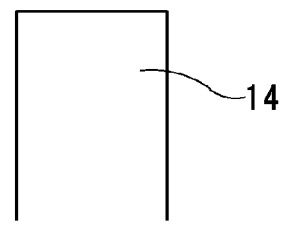

As shown in FIG. 9, if the dimple 23 is formed on the curl portion 22, the first illumination light R is not irradiated to a non-reflection part 23a on an inner surface of the dimple 23. Accordingly, the red reflected light "r" of the first illumination light R enters the imaging device 14 in a state in which the non-reflection part 23a is a shadow. On the other hand, the second illumination light B which is irradiated from the different direction from that of the first illumination light R does not irradiated to a non-reflection part 23b on the inner surface of the dimple 23. Accordingly, the blue reflected light "b" of the second illumination light B enters the imaging device 14 in a state in which the non-reflection part 23b is a shadow. That is to say, the blue reflection light "b" from the non-reflection part 23a and the red reflection light "r" from the non-reflection part 23b enter the imaging device 14.

Since the first illumination light R and the second illumination light B are irradiated simultaneously, as shown in FIG. 9, from the flat part without asperity in the curl portion 22, the reflected light "p" having a mixture of colors is detected. On the other hand, from the inner surface of the dimple 23, the red reflected light "r" and the blue reflected light "b" are detected. Accordingly, it is recognized that the asperity such as the dimple 23 is formed on a part in which the reflected lights "b" and "r" each having one color in accordance with the colors of the illumination lights R and B are detected. Particularly, because the first illumination light R and the second illumination light B are complementary colors to each other, the reflected lights "r" and "b" having one color are clearly detected, so that the asperity can be reliably detected.

As explained above, according to the inspection equipment of the present invention, by irradiating the illumination lights having the different colors from a plurality of directions, the curl portion is correctly specified, the color-figure without the asperity is not detected as defective, and the asperity can be reliably detected. As a result, in the inspection for the mouth section of the bottle-can, the yield is not deteriorated, and it is possible to reliably detect only the defective product which may cause the liquid leakage.

The present invention is not limited to the above-described embodiments and various modifications in the details may be made without departing from the scope of the present invention.

Figure 10:
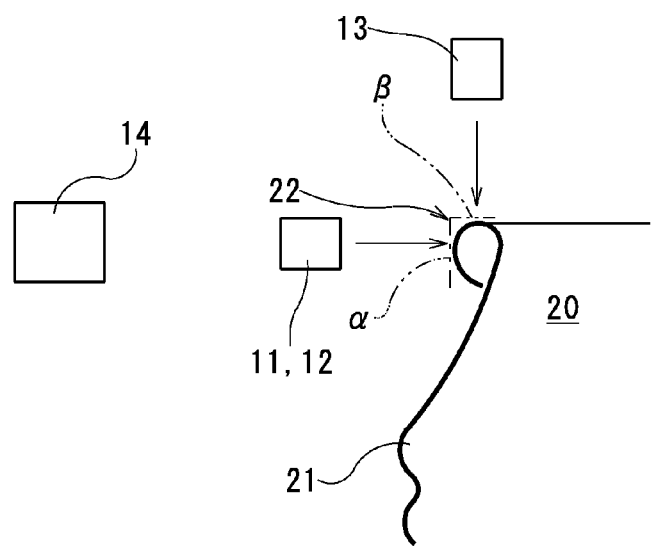
FIG. 10 It is a cross view showing an example in which an imaging area is set on an external circumferential surface of the curl portion in inspection equipment for mouth section is according to the present invention.

For example, in the inspection equipment of the above embodiment, the imaging area to which the first illumination light and the second illumination light are irradiated is set to the top surface of the curl portion, and the third illumination light is set to be irradiated to the external circumferential surface of the curl portion. However, on the contrary to this embodiment, as shown in FIG. 10, the imaging area α may be set to the external circumferential surface of the curl portion 22, and the edge-detection area β may be set to the top surface of the curl portion 22. In this case, the asperity formed on the external circumferential surface of the curl portion 22 can be detected with distinguishing from the color-figure or the like. Also, it is possible to detect the defect such as a deformation in which a height of the top surface of the curl portion 22 is uneven.

Furthermore, in the inspection equipment of the above embodiment, one set of the first illumination device and the second illumination device is provided, and the first illumination light and the second illumination light are irradiated from the outer peripheral side of the mouth section toward the top surface of the curl portion; however, a plurality of sets of the first illumination device and the second illumination device may be provided. For example, if the top surface of the curl portion is bent and protruded, the illumination light is obstructed by the protrusion, so that the inner circumferential of the top surface of the curl portion cannot be illuminated. Accordingly, although the asperity on the external periphery side of the top surface of the curl portion can be detected, it is hard to detect the asperity on the internal peripheral side.

Figure 11:
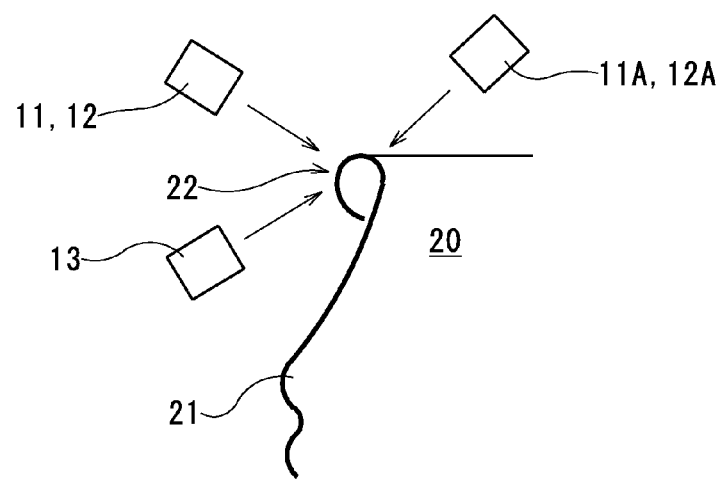
FIG. 11 It is a cross view showing an example in which two sets of first illumination devices and second illumination devices are provided in inspection equipment for mouth section according to the present invention.
Figure 12:
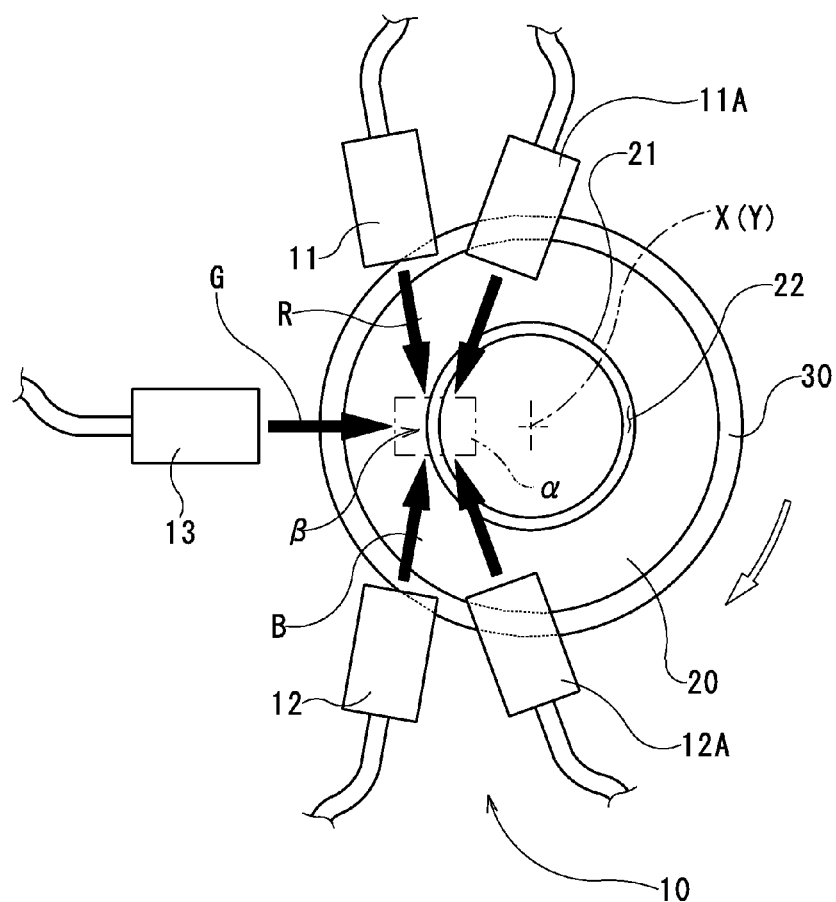
FIG. 12 It is a top view showing the inspection equipment shown in FIG. 11.

In such a case, as shown in FIG. 11 and FIG. 12, in addition to the first illumination device 11 and the second illumination device 12 irradiating the illumination lights toward the top surface of the curl portion 22 from the external circumferential side of the mouth section 21, a second set of a first illumination device 11A and a second illumination device 12A irradiating the illumination lights toward top surface of the curl portion 22 from the internal peripheral side of the mouth section 21 are provided, so that the top surface of the curl portion 22 can be extensively inspected.

INDUSTRIAL APPLICABILITY

By irradiating the illumination lights having the different colors from the different directions, since the mouth section is correctly specified in the inspection image and the color-figure without the asperity is not detected as the defect, the asperity can be reliably detected, so that the yield is not deteriorated and it is possible to reliably eliminate only the defective product which may cause the liquid leakage.

DESCRIPTION OF THE REFERENCE SYMBOLS 10 inspection equipment for mouth section
11, 11A first illumination device
12, 12A second illumination device
13 third illumination device
14 imaging device
20 bottle-can
21 mouth section
22 curl portion
23 dimple
23a, 23b non-reflection part
24 pit
25 flaw
26 bent portion
27 deformation
30 rotating device
31 asperity-recognition device
R first illumination light
B second illumination light
G third illumination light
r red reflected light
b blue reflected light
g green reflected light
p purple reflected light
X can-axis
Y rotating axis
α imaging area
β edge-detection area
E edge position
I inspection image
S scanned image
T top surface

The invention claimed is:

1. Inspection equipment for a mouth section of a bottle-can, with respect to the bottle-can having the cylindrical mouth section in which a curl portion is formed by curling an open end thereof for a cap with a liner to be put on, by taking an image of an imaging area which is set to include a part of the curl portion for detecting an asperity-defect at the curl portion, the inspection equipment comprising:
   a rotating device which holds and rotates the bottle-can around a can-axis;
   a first illumination device which irradiates a first illumination light substantially along a tangential direction of a cylindrical surface of the mouth section toward the curl portion in the imaging area;
   a second illumination device which irradiates a second illumination light having a different light color from that of the first illumination light toward a part in which the first illumination light is irradiated on the curl portion from an opposite side to the first illumination light with the imaging area therebetween along substantially a tangential direction of the cylindrical surface of the mouth section;
   a third illumination device which irradiates a third illumination light having a different light color from that of the first illumination light and the second illumination light toward the part in which the first illumination light and the second illumination light are irradiated on the curl portion along an intersecting direction;
   an imaging device which is disposed toward the imaging area and obtains an inspection image including a first reflected light of the first illumination light, a second reflected light of the second illumination light, and a third reflected light of the third illumination light at the curl portion; and
   an asperity-defect-recognition device which detects an edge position of the curl portion in the inspection image based on a third imaging result of the third reflected light of the third illumination light by following the third reflected light and regarding a position thereof as the edge position of the curl portion, and detects the asperity-defect in a prescribed width from the edge position based on a first imaging result of the first reflected light of the first illumination light and a second imaging result of the second reflected light of the second illumination light existing in the inspection image.

2. The inspection equipment for mouth section of bottle-can according to claim 1, wherein:
   the imaging area is set to include a top surface of the curl portion;
   the first illumination device and the second illumination device are arranged so that the first illumination light and the second illumination light are irradiated to the top surface of the curl portion in the imaging area; and the third illumination device is arranged so that the third illumination light is irradiated to an external circumferential surface of the curl portion which is continued and bent from the part in which the first illumination light and the second illumination light are irradiated.

3. The inspection equipment for mouth section of bottle-can according to claim 1, wherein:

the imaging area is set to include an external circumferential surface of the curl portion;

the first illumination light and the second illumination light are irradiated to the imaging area; and third illumination light is irradiated toward a top surface which is continued and bent from the part in which the first illumination light and the second illumination light are irradiated.

4. The inspection equipment for mouth section of bottle-can according to claim 1, wherein a plurality of sets of the first illumination devices and the second illumination devices are provided.

5. The inspection equipment for mouth section of bottle-can according to claim 2, wherein a plurality of sets of the first illumination devices and the second illumination devices are provided.

6. The inspection equipment for mouth section of bottle-can according to claim 3, wherein a plurality of sets of the first illumination devices and the second illumination devices are provided.

7. The inspection equipment for mouth section of bottle-can according to claim 1, wherein the asperity-defect in the prescribed width from the edge position of the curl portion is detected by detecting the first reflected light and/or the second reflected light.

8. The inspection equipment for mouth section of bottle-can according to claim 1, wherein a direction of the third illumination light is substantially orthogonal to an imaging direction of the imaging device.

9. The inspection equipment for mouth section of bottle-can according to claim 1, wherein an edge-detection area is set to include a part of the curl portion which is continued to and bent from the part which is included in the imaging area, so that the third illumination light is irradiated to the part included in the edge-detection area.

* * * * *